US012077730B2

(12) United States Patent
Champion et al.

(10) Patent No.: US 12,077,730 B2
(45) Date of Patent: Sep. 3, 2024

(54) QUATERNARY AMMONIUM HYDROXIDES OF POLYAMINES

(71) Applicant: Huntsman Petrochemical LLC, The Woodlands, TX (US)

(72) Inventors: Donald H. Champion, The Woodlands, TX (US); David C. Lewis, The Woodlands, TX (US); Juventino Uriarte, The Woodlands, TX (US); Hui Zhou, The Woodlands, TX (US); Ke Zhang, The Woodlands, TX (US); Chai Zheng, The Woodlands, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 266 days.

(21) Appl. No.: 17/270,881

(22) PCT Filed: Jul. 29, 2019

(86) PCT No.: PCT/US2019/043862
§ 371 (c)(1),
(2) Date: Feb. 24, 2021

(87) PCT Pub. No.: WO2020/046515
PCT Pub. Date: Mar. 5, 2020

(65) Prior Publication Data
US 2021/0179972 A1   Jun. 17, 2021

Related U.S. Application Data

(60) Provisional application No. 62/724,849, filed on Aug. 30, 2018.

(51) Int. Cl.
| | |
|---|---|
| *C11D 3/28* | (2006.01) |
| *C11D 3/20* | (2006.01) |
| *C11D 3/30* | (2006.01) |
| *C11D 7/26* | (2006.01) |
| *C11D 7/32* | (2006.01) |
| *G03F 7/42* | (2006.01) |

(52) U.S. Cl.
CPC .............. *C11D 3/30* (2013.01); *C11D 3/20* (2013.01); *C11D 7/26* (2013.01); *C11D 7/3209* (2013.01); *G03F 7/425* (2013.01); *C11D 2111/16* (2024.01); *C11D 2111/22* (2024.01)

(58) Field of Classification Search
CPC ............ C11D 3/20; C11D 7/26; C11D 7/3209
USPC ......................................... 510/504, 505, 506
See application file for complete search history.

(56) References Cited

U.S. PATENT DOCUMENTS

| | | | |
|---|---|---|---|
| 2,096,534 A * | 10/1937 | Bayer et al. ......... | C07D 251/16 544/194 |
| 2,695,314 A * | 11/1954 | Kosmin ................ | C09K 23/00 564/511 |
| 2,717,909 A | 9/1955 | Kosmin | |
| 2,766,288 A * | 10/1956 | Erickson .................. | C10M 5/00 564/295 |
| 3,281,452 A * | 10/1966 | Kapar ..................... | C08G 69/48 521/25 |
| 3,334,138 A * | 8/1967 | Feeman ............. | C08G 73/0226 252/8.61 |
| 6,908,892 B2 | 6/2005 | Yoon et al. | |
| 7,135,445 B2 | 11/2006 | Charm et al. | |
| 7,498,295 B2 | 3/2009 | Fisher et al. | |
| 7,671,001 B2 | 3/2010 | Skee | |
| 7,825,079 B2 | 11/2010 | Suzuki et al. | |
| 8,765,653 B2 | 7/2014 | Tamboli et al. | |
| 9,476,019 B2 | 10/2016 | Nakanishi et al. | |
| 2003/0127024 A1 | 7/2003 | Heiberger et al. | |
| 2005/0025066 A1 | 11/2005 | Takashima | |

FOREIGN PATENT DOCUMENTS

| | | |
|---|---|---|
| CN | 107586589 A | 1/2018 |
| GB | 1028561 A | 5/1966 |
| JP | 59-134752 A | 8/1984 |
| JP | 2011-507236 A | 3/2011 |
| KR | 20170007621 A | 1/2017 |
| WO | 2001053419 A1 | 7/2001 |
| WO | 2006/056298 | 6/2006 |
| WO | 2009076201 A1 | 6/2009 |
| WO | WO-2019222127 A1 * 11/2019 ........ B01J 31/0237 |

OTHER PUBLICATIONS

International Search Report received in corresponding PCT Application No. PCT/US2019/043862 completed Nov. 10, 2019 and dated Dec. 3, 2019.
Written Opinion received in corresponding PCT Application No. PCT/US2019/043862 completed Nov. 10, 2019 and dated Dec. 3, 2019.
Burgen A. S. V. et al.: "The Specificity of Brain Choline Acetylase", British Journal of Pharmacology and Chemotherapy., vol. 11, No. 3, Sep. 1, 1956 (Sep. 1, 1956), pp. 308-312.
Fujiwara Saki et al.: "Design of Dictation-Type Amino Acid Ionic Liquids and Their Application to Self-Assembly Media of Amphiphiles", Bulletin of the Chemical Society of Japan, vol. 91, No. 1, Jan. 15, 2018 (Jan. 15, 2018), pp. 1-5.
So Han Kim et al.: "Dinuclear Aluminum Complexes as Catalysts for Cycloaddition of CO2 to Epoxides", ORGANOMETALLICS, vol. 33, No. 11, May 29, 2014 (May 29, 2014), pp. 2770-2775.
CAS: 13111-44-9", STN Registry Database, published on Nov. 16, 1984.
Extended European Search Report issued Jun. 7, 2022, in corresponding European Application No. 19856217.5.
Japanese Office Action issued Jan. 25, 2023, in corresponding Japanese Application No. 2021-510429 (English translation enclosed herewith).

* cited by examiner

*Primary Examiner* — Gregory R Delcotto
(74) *Attorney, Agent, or Firm* — HUNTSMAN PETROCHEMICAL LLC; Aleece Hayes

(57) ABSTRACT

The present disclosure provides a quaternary ammonium hydroxide solution comprising a reaction product of a polyamine and an organic oxirane. The quaternary ammonium hydroxide solution may be used in various applications, such as in removing chemical residue from a metal or dielectric surface.

18 Claims, No Drawings

QUATERNARY AMMONIUM HYDROXIDES OF POLYAMINES

CROSS REFERENCE TO RELATED APPLICATIONS

The present application is the National Phase of International Application PCT/US2019/043862 filed Jul. 29, 2019 which designated the U.S. and which claims priority to U.S. Provisional Patent Application Ser. No. 62/724,849, filed Aug. 30, 2018, the entire contents of which is hereby expressly incorporated herein by reference.

STATEMENT REGARDING FEDERALLY SPONSORED RESEARCH OR DEVELOPMENT

Not applicable.

FIELD

The present disclosure generally relates to a quaternary ammonium hydroxide solution comprising the reaction product of a polyamine and an organic oxirane. The quaternary ammonium hydroxide solution may be used in various applications, including, but not limited to, etching, cleaning, polishing and pattern developing for metallic and dielectric surfaces.

BACKGROUND

The fabrication of integrated circuits and other electronic devices, such as photovoltaic cells, incorporates various processing steps that may involve a number of toxic, flammable, explosive and/or environmentally unfriendly chemicals. Many of these chemicals are also widely used for metallic or non-metallic surfaces in a variety of other applications including exterior aircraft cleaning, metal parts processing and engine maintenance.

Ammonium hydroxides, for example, tetramethylammonium hydroxide, have traditionally been used in etching, cleaning, polishing and pattern developing as described in:

U.S. Pat. No. 7,825,079 which discloses a composition comprising tetramethylammonium hydroxide and a chelant for use in removing photoresist or post etch residue;

U.S. Pat. No. 7,671,001 which discloses a composition comprising tetramethylammonium hydroxide and a metal corrosion inhibitor for use in cleaning semiconductor wafer substrates;

U.S. Pat. No. 7,498,295 which discloses a composition comprising tetramethylammonium hydroxide, a chelant and a corrosion inhibitor for use after chemical mechanical planarization of semiconductor substrates; and WO 2006/056298 which discloses a composition comprising tetramethylammonium hydroxide, dimethyl sulfoxide, ethylene glycol and water for use in cleaning microelectronic substrates.

Although tetramethylammonium hydroxide is known to be highly effective, it has been found to be highly toxic to the nervous system. Accordingly, safer alternatives to this chemical are continuously being sought. One such alternative that has been recently used is choline hydroxide as described in:

U.S. Pat. No. 8,765,653 which discloses a composition comprising copolymers of acrylamido-methyl-propane sulfonate, acrylic acid-2-acrylamido-2-methylpropane sulfonic acid copolymer and mixtures thereof, a non-acetlyinic surfactant and choline hydroxide for use in removing residue in semiconductor manufacturing processes; and U.S. Pat. No. 7,135,445 which discloses a composition comprising bis-choline hydroxide or tris-choline hydroxide, a solvent and a corrosion inhibitor for use in cleaning fluxes and resist materials from microcircuits.

While choline hydroxide has several advantages over tetramethylammonium hydroxide, such as low toxicity, relatively low cost, ease of manufacture and biodegradable, it suffers from having a serious odor problem during use and can decompose to give colored solutions and precipitates. Thus, it would be desirable to develop new compositions that are just as effective as state of the art compositions containing tetramethylammonium hydroxide or choline hydroxide, but do not exhibit the toxicity, odor or color problems described above.

SUMMARY

The present disclosure is directed to a quaternary ammonium hydroxide solution comprising a reaction product of (i) a polyamine and (ii) an organic oxirane.

The quaternary ammonium hydroxide of the present disclosure may be used in a variety of applications, such as in compositions for use in the removal of chemical residue from a metallic surface or dielectric surface.

DETAILED DESCRIPTION

If appearing herein, the term "comprising" and derivatives thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, except those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical objects of the article. By way of example, "a polyamine" means one polyamine or more than one polyamine. The phrases "in one embodiment", "according to one embodiment" and the like generally mean the particular feature, structure, or characteristic following the phrase is included in at least one embodiment of the present disclosure, and may be included in more than one embodiment of the present disclosure. Importantly, such phrases do not necessarily refer to the same embodiment. If the specification states a component or feature "may", "can", "could", or "might" be included or have a characteristic, that particular component or feature is not required to be included or have the characteristic.

The term "about" as used herein can allow for a degree of variability in a value or range, for example, it may be within 10%, within 5%, or within 1 of a stated value or of a stated limit of a range.

Values expressed in a range format should be interpreted in a flexible manner to include not only the numerical values explicitly recited as the limits of the range, but to also include all of the individual numerical values or sub-ranges encompassed within that range as if each numerical value and sub-range is explicitly recited. For example, a range from 1 to 6, should be considered to have specifically disclosed sub-ranges, such as, from 1 to 3 or from 2 to 4 or from 3 to 6, etc., as well as individual numbers within that range, for example, 1, 2, 3, 4, 5, and 6. This applies regardless of the breadth of the range.

In the methods and processes described herein, the steps may be carried out in any order, except when a temporal or operational sequence is explicitly recited. Furthermore, specified steps may be carried out concurrently unless explicit claim language recites that they be carried out separately.

The term "substantially free" refers to a composition or mixture in which a particular compound is present in an amount that has no material effect on the composition or mixture. For example, "substantially free of choline hydroxide" means that choline hydroxide may be included in the composition or mixture in an amount that does not materially affect the odor or color of the composition or mixture. It is within the ability of one skilled in the art with the benefit of this disclosure to determine if and whether an amount of a compound has a material effect on the composition. In some embodiments, substantially free may be less than 2 wt. % or less than 1 wt. % or less than 0.5 wt. % or less than 0.1 wt. % or less than 0.05 wt. % or even less than 0.01 wt. %, based on the total weight of the composition. In some embodiments, substantially free means the particular compound is not present in any amount (i.e. 0.0 wt. %) in the respective composition.

The term "alkyl" as used herein refers to a branched or unbranched saturated hydrocarbon group having 1 to 30 carbon atoms, such as methyl ("Me"), ethyl ("Et"), n-propyl, isopropyl, n-butyl, isobutyl, t-butyl, octyl, decyl, tetradecyl, hexadecyl, eicosyl, tetracosyl and the like. In some aspects, alkyl groups herein may contain from 1 to 12 carbon atoms. The term "lower alkyl" refers to an alkyl group having from 1 to 7 carbon atoms, or in some aspects from 1 to 4 carbon atoms. The term "higher alkyl" refers to an alkyl group having more than 7 carbon atoms.

The term "organic oxirane" refers to a compound having a formula

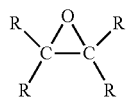

where each R is the same or different and is hydrogen, an alkyl group having 1 to 6 carbon atoms, an unsaturated alkyl group, an aryl group an aralkyl group or one or more R groups form a cyclic structure containing 3 to 12 carbon atoms and in some embodiments the R groups may contain one or more oxygen atoms. Examples of alkylene oxides, a subclass of organic oxiranes, that may be used include, but are not limited to, methylene, ethylene, propylene, butylene, pentylene and hexylene oxides.

The term "alkyloxyalkyl" refers to an alkyl group substituted with an —O-alkyl group.

The term "aryl" refers to a $C_6$-$C_{14}$ mono- or polycyclic aromatic ring system including, but not limited to, phenyl, naphthyl, phenanthryl, anthracyl, indenyl, azulenyl, biphenyl, biphenylenyl and fluorenyl groups.

The term "aralkyl" refers to an alkyl group substituted by an aryl group.

The term "cycloalkyl" refers to a saturated cyclic alkyl group having 3 to 12 carbon atoms, such as cyclopropyl, cyclohexyl and cyclooctyl which may have suitable substituents on the ring.

The term "optional" or "optionally" means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and alkyl where there is substitution.

The term "polyamine" refers to a compound having two or more amine groups per molecule wherein at least one amine group is a tertiary amine group or is converted to such an amine group in situ. For example N,N,N'N'-tetrakis(2-hydroxyethyl)ethylenediamine may be prepared in situ by reaction of ethylenediamine and ethylene oxide and then may be further ethoxylated (i.e. reacted with an organic oxirane) to form a quaternary ammonium hydroxide.

As mentioned above, in the electronics and metal working industries, ammonium hydroxides are generally used in processes such as in etching, cleaning, polishing and pattern developing metallic and dielectric surfaces. While the effects of these ammonium compounds are thought to be attributed to the presence of hydroxide ions acting at the metal or dielectric surfaces, the design of the organic ammonium ions can greatly affect the performance of these hydroxides. Applicant has surprisingly discovered a number of quaternary ammonium hydroxides that exhibit high reactivity on metal or dielectric surfaces. In addition, the quaternary ammonium hydroxides of the present disclosure are relatively non-toxic and substantially odor-free and may be easily designed to offer a range of reactivity's for one to choose from when specific reaction rates are needed during a wet processing step or a particular type or mixture of metal or dielectric surface is encountered. The quaternary ammonium hydroxides of the present invention may also be employed for organic photoresist development, etching or removal of unwanted organic or other residue.

Accordingly, in a first embodiment there is provided a quaternary ammonium hydroxide solution comprising a reaction product of a polyamine and an organic oxirane.

A wide variety of polyamines may be employed as long as they have at least one tertiary amine group (or can form a tertiary amine in situ) which is capable of forming a quaternary ammonium group. In one embodiment, the quaternary ammonium hydroxide may be derived from a non-hydroxylated polyamine, a hydroxylated polyamine or a mixture thereof.

In one embodiment, the nonhydroxylated polyamine may be a compound having a formula:

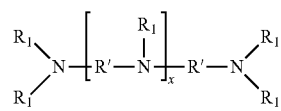

where each $R_1$ is the same or different and is hydrogen, an alkyl group, a cycloalkyl group, an aryl group, an alkyloxyalkyl group, a hydroxylated alkyl group or a hydroxylated alkyloxyalkyl group in such a combination that at least one tertiary nitrogen is formed; x is 0 or an integer of at least 1, for example, 1 to 10 or 1 to 3; and, each R' is the same or different and is an alkyl group with at least 2, for example, 2 to 10 carbon atoms or 2 to 5 carbon atoms, an aryl group, an alkaryl group, an unsaturated hydrocarbyl, or may contain O or N in combination with C and H and further may form a cyclic structure. In some embodiments, two of the $R_1$ groups may be joined to form a cyclic amine, such as morpholines and piperidines and alkyl derivatives such as N-alkyl morpholines and N-alkyl piperidines and imidazolines. In some embodiments, the R' groups may form a cyclic or heterocyclic or aromatic ring, such as morpholines, piperazines piperidines, imidazolines, or phenylene.

In another embodiment, the hydroxylated polyamine may be a compound having a formula:

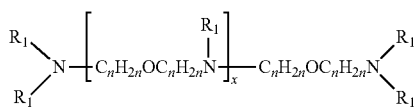

or a compound having the formula:

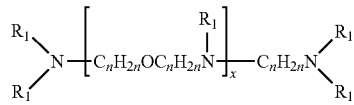

where each $R_1$ is the same or different and is hydrogen, an alkyl group, a cycloalkyl group, an aryl group, an alkyloxy-alkyl group, a hydroxylated alkyl group or a hydroxylated alkyloxyalkyl group in such a combination that at least one tertiary nitrogen is formed; x is 0 or an integer of at least 1, for example, 1 to 10 or 1 to 3; and, n is an integer of at least 2, for example, 2 to 10 or 2 to 5. In some embodiments, two of the $R_1$ groups may be joined to form a cyclic amine, such as morpholines and piperidines and alkyl derivatives such as N-alkyl morpholines and N-alkyl piperidines and imidazolines.

Examples of the above polyamines may include, but are not limited to, N,N,N',N'-tetramethylethylenediamine, N,N,N',N'-tetraethylethylenediamine, N,N,N',N'', N''-pentamethyldiethylenetriamine, N,N,N',N'-tetramethylpropane-1,3-diamine, N,N,N',N'',N'''-pentamethyl dipropylenetriamine, N,N,N',N'-tetramethylpropane-1,3-diamine, N,N,N',N'-tetramethylbutane-1,4-diamine, N,N,N',N'-tetramethylhexane-1,6-diamine, N,N,N',N'-tetrakis(2-hydroxyethyl)ethylenediamine, 1,1,4,7,10,10-hexamethyl triethylenetetramine, N,N,N',N'-tetrakis(2-hydroxypropyl)ethylenediamine, bis(N, N-dimethylaminoethyl)ether and bis(2-dimethylaminoethyl) ether, bis(3-dimethylaminopropyl) ether, bis(2-morpholinoethyl) ether, triethylenediamine, methyltriethylenediamine, ethyltriethylenediamine, dimethyltriethylenediamine, N,N,N-tris(3-dimethylaminopropyl)amine, bis(2-dimethylaminoethyl)amine N,N'-bis(2-aminoethyl)piperazine, N, N'-bis(3-aminopropyl)piperazine and mixtures thereof.

In one embodiment, the organic oxirane is a compound having the formula

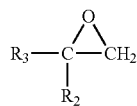

where $R_2$ and $R_3$ are the same or different and are hydrogen, an alkyl group having 1 to 12 carbon atoms, an unsaturated hydrocarbyl, an aryl group having 6 to 18 carbon atoms, an aralkyl group having 6 to 18 carbon atoms or the $R_2$ and $R_3$ groups may form a cyclic structure containing 3 to 12 carbon atoms. In some embodiments, the $R_2$ and $R_3$ groups may further contain one or more oxygen atoms. Examples of organic oxiranes may include, but are not limited to, ethylene oxide, propylene oxide, 1,2-butylene oxide, 1,2-pentane oxide, styrene oxide, the dioxides of dienes, for example, butadiene epoxide and mixtures thereof. Examples of other organic oxirane compounds are cyclohexene oxide, glycidol, allyl glycidyl ether, phenyl glycidyl ether, alkyl glycidyl ether, styrene oxide.bicyclo[2.2.1]heptene oxide and bicyclo[2.2.2]octene oxide.

The reaction of an organic oxirane (for e.g. an alkylene oxide) with a basic nitrogen atom to form a quaternary moiety is well known to those skilled in the art, and needs little elaboration. Thus, in one embodiment, the polyamine is reacted with the organic oxirane in the presence of water. The polyamine may be mixed with water and the system may then be pressurized. The organic oxirane may then be added in a molar ratio of at least about 1:1 to the polyamine. In some embodiments the organic oxirane may be reacted with an amine in the presence of least a stoichiometric amount of water to form the quaternary ammonium hydroxide and in the presence of an organic solvent. In some embodiments, the molar ratio may be in the range from about 1:1 to about 3N:1 organic oxirane to polyamine or from about 1:1 to about 1.5N:1 organic oxirane to polyamine where N is the number of amine groups in the starting compound. For example, for a triamine such as pentamethyldiethylenetriamine (PMDETA), three moles of an organic oxirane with one oxirane per molecule per PMDETA would be N moles of organic oxirane. In some embodiments the amount of organic oxirane to convert any primary or secondary amines to tertiary amine and an additional amount of oxirane to polyamine in a molar ratio of 1:1 to about 3N:1 organic oxirane to polyamine or from about 1:1 to about 1.5N:1 organic oxirane to polyamine where N is the number of amine groups in the starting compound. The reaction may be carried out at a temperature less than about 70° C., for example from about 40° C. to about 50° C., with continuous stirring and its completion may be signaled by a drop in pressure to about atmospheric pressure or the ammonium quat content may be determined by potentiometric titration using a strong acid, such as HCl.

The quaternary ammonium hydroxide solution may comprise any suitable concentration of amine nitrogen's that are quaternized. Thus, in one embodiment, the concentration of quaternized amine in the quaternary ammonium hydroxide solution may range from about 1% by weight to about 80% by weight, based on the total amount of the quaternary ammonium hydroxide solution. In other embodiments, the concentration of quaternized amine nitrogen's in the quaternary ammonium hydroxide solution may range from about 10% by weight to about 70% by weight, or from about 35% by weight to about 65% by weight, or from about 40% by weight to about 60% by weight, or from about 45% by weight to about 55% by weight, based on the total weight of the quaternary ammonium hydroxide solution.

In another embodiment, the products of the present disclosure (i.e. quaternary ammonium hydroxide solution) may comprise a quaternary ammonium hydroxide with at least about 1% of total quat molecules containing more than one quaternary ammonium hydroxide group. In other embodiments, the products of the present disclosure may comprise a quaternary ammonium hydroxide with at least about 2.5% of total quat molecules containing more than one quaternary ammonium hydroxide group or with at least about 5% of total quat molecules containing more than one quaternary ammonium hydroxide group or with at least about 10% of total quat molecules containing more than one quaternary ammonium hydroxide group or with at least about 15% of total quat molecules containing more than one quaternary ammonium hydroxide group or with at least about 20% of total quat molecules containing more than one quaternary ammonium hydroxide group or with at least about 25% of total quat molecules containing more than one quaternary ammonium hydroxide group or with at least about 30% of total quat molecules containing more than one quaternary ammonium hydroxide group or with at least about 35% of total quat molecules containing more than one quaternary ammonium hydroxide group or with at least about 40% of total quat molecules containing more than one quaternary ammonium hydroxide group.

The quaternary ammonium hydroxide solution of the present disclosure may be used in various applications. Thus, in a second aspect there is provided a composition for removing chemical residues from a metal or dielectric surface comprising the quaternary ammonium hydroxide solution of the present disclosure. In some embodiments, the composition may comprise at least about 0.1% by weight, or at least about 0.5% by weight, or at least about 1% by weight, or at least about 2% by weight, or at least about 5% by weight, or at least about 7% by weight, or at least about 10% by weight, of the quaternary ammonium hydroxide solution of the present disclosure, where the by weight is based on the total weight of the composition. In other embodiments, the composition may comprise less than about 20% by weight, or less than about 15% by weight, or less than about 10% by weight of the quaternary ammonium hydroxide solution of the present disclosure, where the % by weight is based on the total weight of the composition.

In some particular embodiments, the composition may be substantially free of choline hydroxide, tetramethylammonium hydroxide or both. In other embodiments, the composition may be substantially free of at least one or all of the etchants described below.

In addition to the quaternary ammonium hydroxide solution of the present disclosure, the composition may further comprise a solvent, a chelating agent, an oxidizing agent, a metal corrosion inhibitor, an etchant, a low-k passivating agent, a silicon-containing compound, a surfactant and combinations thereof.

The solvent may include, but is not limited to, water, at least one water-miscible organic solvent, or a combination thereof. For example, the solvent can comprise at least one species selected from the group consisting of water, methanol, ethanol, isopropanol, butanol, pentanol, hexanol, 2-ethyl-1-hexanol, heptanol, octanol, ethylene glycol, propylene glycol, butylene glycol, hexylene glycol, butylene carbonate, ethylene carbonate, propylene carbonate, butyrolactone, butyrolactam, choline bicarbonate, dipropylene glycol, dimethylsulfoxide, sulfolane, tetrahydrofuran, tetrahydrofurfuryl alcohol (THFA), 1,2-butanediol, 1,4-butanediol, tetramethyl urea, N, N'-dimethylimidazolidinone (dimethylethylene urea), diethylene glycol monomethyl ether, triethylene glycol monomethyl ether, diethylene glycol monoethyl ether, triethylene glycol monoethyl ether, ethylene glycol monopropyl ether, ethylene glycol monobutyl ether, diethylene glycol monobutyl ether, triethylene glycol monobutyl ether, ethylene glycol monohexyl ether, diethylene glycol monohexyl ether, ethylene glycol phenyl ether, propylene glycol methyl ether, dipropylene glycol methyl ether (DPGME), tripropylene glycol methyl ether (TPGME), dipropylene glycol dimethyl ether, dipropylene glycol ethyl ether, propylene glycol n-propyl ether, dipropylene glycol n-propyl ether (DPGPE), tripropylene glycol n-propyl ether, propylene glycol n-butyl ether, dipropylene glycol n-butyl ether, tripropylene glycol n-butyl ether, propylene glycol phenyl ether, ethylene glycol dimethyl ether, diethylene glycol dimethyl ether, 2,3-dihydrodecafluoropentane, ethyl perfluorobutylether, methyl perfluorobutylether, alkyl carbonates, 4-methyl-2-pentanol, N-methylpyrrolidinone (NMP), hexamethylphosphoram ide, N, N'-dimethylacetamine (DMAC), N,N-dimethylformamide (DMF), and combinations thereof. In some embodiments, the solvent comprises water, in other embodiments, deionized water. The solvent may be present in an amount of from about 20% by weight to about 99.9% by weight, or from about 30% by weight to about 98% by weight, or even from about 50% by weight to about 95% by weight, where the % by weight is based on the total weight of the composition.

The chelating agent may include, but is not limited to, β-diketonate compounds such as acetylacetonate, 1,1,1-trifluoro-2,4-pentanedione, and 1,1,1,5,5,5-hexafluoro-2,4-pentanedione; amines and amino acids such as glycine, serine, proline, leucine, alanine, asparagine, aspartic acid, glutamine, valine, and lysine; polyprotic acids selected from the group consisting of iminodiacetic acid (IDA), malonic acid, oxalic acid, succinic acid, boric acid, nitrilotriacetic acid, malic acid, citric acid, acetic acid, maleic acid, ethylenediaminetetraacetic acid (EDTA), EDTA-2N $H_3$ (ethylenediaminetetraacetic acid diammonium salt), (1,2-cyclohexylenedinitrilo)tetraacetic acid (CDTA), diethylenetriamine pentaacetic acid (DTPA), 2-phosphonobutane-1,2,4-tricarboxylic acid (PBTCA), ethylendiamine disuccinic acid, and propylenediamine tetraacetic acid; phosphonic acid; phosphonic acid derivatives such as hydroxyethylidene diphosphonic acid (HEDP), 1-hydroxyethane-1,1-diphosphonic acid, nitrilo-tris(methylenephosphonic acid) (NTMP), amino tri(methylene phosphonic acid), diethylenetriamine penta(methylene phosphonic acid), ethylenediamine tetra(methylene phosphonic acid) (EDTMPA); ethylenediamine; 2,4-pentanedione; benzalkonium chloride; 1-imidazole; tetraglyme; pentamethyldiethylenetriamine (PMDETA); 1,3,5-triazine-2,4,6-thithiol trisodium salt solution; 1,3,5-triazine-2,4,6-thithiol triammonium salt solution; sodium diethyldithiocarbamate; disubstituted dithiocarbamates and combinations thereof. The chelating agent may be present in an amount of from about 0.01% by weight to about 1% by weight, where the % by weight is based on the total weight of the composition.

The oxidizing agent may include, but is not limited to, hydrogen peroxide ($H_2O_2$), $FeCl_3$, $FeF_3$, $Fe(NO_3)_3$, $Sr(NO_3)_2$, $CoF_3$, $MnF_3$, oxone ($2KHSO_5.KHSO_4.K_2SO_4$), periodic acid, iodic acid, vanadium (V) oxide, vanadium (IV,V) oxide, ammonium vanadate, ammonium polyatomic salts (e.g., ammonium peroxomonosulfate, ammonium chlorite ($NH_4ClO_2$), ammonium chlorate ($NH_4ClO_3$), ammonium iodate ($NH_4IO_3$), ammonium nitrate ($NH_4NO_3$), ammonium perborate ($NH_4BO_3$), ammonium perchlorate ($NH_4ClO_4$), ammonium periodate ($NH_4IO_4$), ammonium persulfate (($NH_4)_2S_2O_8$), ammonium hypochlorite ($NH_4ClO$)), ammonium hypobromite, ammonium tungstate (($NH_4)_{10}H_2(W_2O_7)$), sodium polyatomic salts (e.g., sodium persulfate ($Na_2S_2O_8$), sodium hypochlorite (NaClO), sodium perborate, sodium hypobromite (NaBrO)), potassium polyatomic salts (e.g., potassium iodate ($KIO_3$), potassium permanganate ($KMnO_4$), potassium persulfate, nitric acid (HNO$_3$), potassium persulfate (K$_2$S$_2$O$_8$), potassium hypochlorite (KClO)), tetramethylammonium polyatomic salts (e.g., tetramethylammonium chlorite ((N(CH$_3$)$_4$)ClO$_2$), tetramethylammonium chlorate ((N(CH$_3$)$_4$)ClO$_3$), tetramethylammonium iodate ((N(CH$_3$)$_4$)IO$_3$), tetramethylammonium perborate ((N(CH$_3$)$_4$)BO$_3$), tetramethylammonium perchlorate ((N(CH$_3$)$_4$)ClO$_4$), tetramethylammonium periodate ((N(CH$_3$)$_4$)IO$_4$), tetramethylammonium persulfate ((N(CH$_3$)$_4$)S$_2$O$_8$)), tetrabutylammonium polyatomic salts (e.g., tetrabutylammonium peroxomonosulfate), peroxomonosulfuric acid, ferric nitrate (Fe(NO$_3$)$_3$), urea hydrogen peroxide ((CO(NH$_2$)$_2$)H$_2$O$_2$), peracetic acid (CH$_3$(CO)OOH), 1,4-benzoquinone, toluquinone, dimethyl-1,4-benzoquinone, chloranil, alloxan, N-methylmorpholine N-oxide, trimethylamine N-oxide, and combinations thereof. When the oxidizing agent is a salt it can be hydrated or anhydrous. The oxidizing agent may be present in an amount of from about 10% by weight to about 40% by weight, where the % by weight is based on the total weight of the composition.

Metal corrosion inhibitors contemplated herein include, but are not limited to, 5-amino-1,3,4-thiadiazole-2-thiol (ATDT), 2-amino-5-ethyl-1,3,4-thiadiazole, benzotriazole (BTA), 1,2,4-triazole (TAZ), tolyltriazole, 5-methyl-benzotriazole (m BTA), 5-phenyl-benzotriazole, 5-nitro-benzotriazole, benzotriazole carboxylic acid, 3-amino-5-mercapto-1,2,4-triazole, 1-amino-1,2,4-triazole, hydroxybenzotriazole, 2-(5-amino-pentyl)-benzotriazole, 1-amino-1,2,3-triazole, 1-amino-5-methyl-1,2,3-triazole, 3-amino-1,2,4-triazole (3-ATA), 3-mercapto-1,2,4-triazole, 3-isopropyl-1,2,4-triazole, 5-phenylthiol-benzotriazole, halo-benzotriazoles (halo=F, Cl, Br or I), naphthotriazole, 2-mercaptobenzimidazole (MBI), 2-mercaptobenzothiazole, 4-methyl-2-phenylimidazole, 2-mercaptothiazoline, 5-amino-1,2,4-triazole (5-ATA), sodium dedecyl sulfate (SDS), 3-amino-5-mercapto-1,2,4-triazole, 3,5-diamino-1,2,4-triazole, pentylenetetrazole, 5-phenyl-1H-tetrazole, 5-benzyl-1H-tetrazole, 5-methyltetrazole, 5-mercapto-1-methyltetrazole, 1-phenyl-1H-tetrazole-5-thiol, 2-benzylpyridine, succinimide, 2,4-diamino-6-methyl-1,3,5-triazine, thiazole, triazine, methyltetrazole, 1,3-dimethyl-2-imidazolidinone, 1,5-pentamethylenetetrazole, 1-phenyl-5-mercaptotetrazole, diaminomethyltriazine, imidazoline thione, 4-methyl-4H-1,2,4-triazole-3-thiol, 4-amino-4H-1,2,4-triazole, 3-amino-5-methylthio-1H-1,2,4-triazole, benzothiazole, imidazole, benzimidazole, 2-aminobenzimidazole, 1-methylimidazole, indiazole, adenine, succinimide, adenosine, carbazole, saccharin, uric acid, and benzoin oxime. Additional corrosion inhibitors include cationic quaternary salts such as benzalkonium chloride, benzyldimethyldodecylammonium chloride, myristyltrimethylammonium bromide, dodecyltrimethylammonium bromide, hexadecylpyridinium chloride, benzyldimethylphenylammonium chloride, hexadecyltrimethylammonium p-toluenesulfonate, hexadecyltrimethylammonium hydroxide, 1-methyl-1'-tetradecyl-4,4'-bipyridium dichloride, alkyltrimethylammonium bromide, amprolium hydrochloride, benzethonium hydroxide, benzethonium chloride, benzyldimethylhexadecylammonium chloride, benzyldimethyltetradecylammonium chloride, benzyldodecyldimethylammonium bromide, benzyldodecyldimethylammonium chloride, cetylpyridinium chloride, choline p-toluenesulfonate salt, dimethyldioctadecylammonium bromide, dodecylethyldimethylammonium bromide, dodecyltrimethylammonium chloride, decyltrimethylammonium chloride (DTAC), ethylhexadecyldimethylammonium bromide, Girard's reagent, hexadecyl(2-hydroxyethyl)dimethylammonium dihydrogen phosphate, dexadecylpyridinium bromide, hexadecyltrimethylammonium bromide, hexadecyltrimethylammonium chloride, methylbenzethonium chloride, N,N',N'-polyoxyethylene (10)-N-tallow-1,3-diaminopropane liquid, oxyphenonium bromide, tetraheptylammonium bromide, tetrakis(decyl)ammonium bromide, thonzonium bromide, tridodecylammonium chloride, trimethyloctadecylammonium bromide, 1-methyl-3-n-octylimidazolium tetrafluoroborate, 1-decyl-3-methylimidazolium tetrafluoroborate, 1-decyl-3-methylimidazolium chloride, tridodecylmethylammonium bromide, dimethyldistearylammonium chloride, cetyltrimethylammonium bromide, myristyltrimethylammonium bromide, and hexamethonium chloride. Other corrosion inhibitors include non-ionic surfactants such as poly(ethylene glycol), poly(propylene glycol), ethylene oxide/propylene oxide block copolymers such as polyoxyethylene (20) sorbitan monooleate, polyoxyethylene (20) sorbitan monopalmitate, polyoxyethylene (20) sorbitan monolaurate, polyoxypropylene/polyoxyethylene block copolymers, anionic surfactants such as dodecylbenzenesulfonic acid, sodium dodecylbenzenesulfonate, dodecylphosphonic acid (DDPA), bis(2-ethylhexyl)phosphate, benzylphosphonic acid, diphenylphosphinic acid, 1,2-ethylenediphosphonic acid, phenylphosphonic acid, cinnamic acid and combinations thereof. The metal corrosion inhibitor may be present in an amount of from about 0.01% by weight to about 2% by weight, where the % by weight is based on the total weight of the composition.

The etchant may include, but is not limited to, HF, ammonium fluoride, tetrafluoroboric acid, hexafluorosilicic acid, other compounds containing B—F or Si—F bonds, tetrabutylammonium tetrafluoroborate (TBA-BF$_4$), tetraalkylammonium fluoride (NR$_a$R$_b$R$_c$R$_d$F), strong bases such as tetraalkylammonium hydroxide (NR$_a$R$_b$R$_c$R$_d$OH), where R$_a$, R$_b$, R$_c$ and R$_d$ may be the same as or different from one another and may be selected from the group consisting of hydrogen, straight-chained or branched C$_1$-C$_6$ alkyl groups (e.g., methyl, ethyl, propyl, butyl, pentyl, hexyl), C$_1$-C$_6$ alkoxy groups (e.g., hydroxyethyl, hydroxypropyl) substituted or unsubstitued aryl groups (e.g., benzyl), weak bases, and combinations thereof. In some embodiments, the fluoride source comprises tetrafluoroboric acid, hexafluorosilicic acid, H$_2$ZrF$_6$, H$_2$TiF$_6$, HPF$_6$, ammonium fluoride, tetramethylammonium fluoride, tetramethylammonium hydroxide, ammonium hexafluorosilicate, ammonium hexafluorotitanate, or a combination of ammonium fluoride and tetramethylammonium fluoride. Alternatively, or in addition to fluoride sources, the etchant may include a strong base such as tetramethylammonium hydroxide (TMAH), tetraethylammonium hydroxide (TEAH), tetrapropylammonium hydroxide (TPAH), tetrabutylammonium hydroxide (TBAH), benzyltrimethylammonium hydroxide (BTMAH), potassium hydroxide, ammonium hydroxide, benzyltriethylammonium hydroxide (BTEAH), tetrabutylphosphonium hydroxide (TBPH), (2-hydroxyethyl) trimethylammonium hydroxide (choline hydroxide), (2-hydroxyethyl) triethylammonium hydroxide, (2-hydroxyethyl) tripropylammonium hydroxide, (1-hydroxypropyl) trimethylammonium hydroxide, ethyltrimethylammonium hydroxide, diethyldimethylammonium hydroxide (DEDMAH), tris(2-hydroxyethyl) methyl ammonium hydroxide (THEMAH), 1,1,3,3-tetramethylguanidine (TMG), potassium hydroxide, guanidine carbonate, arginine, and combinations thereof. If choline hydroxide is used, it is known by the person skilled in the art that the commercial product often includes a small amount of stabilizer to minimize the degradation of the choline hydroxide to undesired byproducts. Choline hydroxide stabilizers are known in the art and include, but are not limited to, formaldehyde, hydroxylamine, sulfites, and hydrides. Weak bases contemplated include, but are not limited to, ammonium hydroxide, monoethanolamine (MEA), diethanolamine (DEA), triethanolamine (TEA), ethylenediamine, cysteine, and combinations thereof. The additional etchant may be present in an amount of from about 0.01% by weight to about 15% by weight, where the % by weight is based on the total weight of the composition.

The low-k passivating agent may include, but is not limited to, boric acid, borate salts, such as ammonium pentaborate, sodium tetraborate, 3-hydroxy-2-naphthoic acid, malonic acid, iminodiacetic acid and combinations thereof. The low-k passivating agent may be present in an amount of from about 0.01% by weight to about 2% by weight, where the % by weight is based on the total weight of the composition.

The silicon-containing compounds include, but are not limited to, methyltrimethoxysilane, dimethyldimethoxysilane, phenyltrimethoxysilane, tetraethoxysilane (TEOS), N-propyltrimethoxysilane, N-propyltriethoxysilane, hexyltrimethoxysilane, hexyltriethoxysilane, and combinations thereof. Other silicon-containing compounds that can be used instead or in addition to the alkoxysilanes above include ammonium hexaflurorosilicate, sodium silicate, potassium silicate, tetramethyl ammonium silicate (TMAS), and combinations thereof. The silicon-containing compound may be present in an amount of from about 0.001% by weight to about 2% by weight, where the % by weight is based on the total weight of the composition.

The surfactant that can be added to the aqueous composition may be an oxidation resistant, fluorinated anionic surfactant. Anionic surfactants contemplated include, but are not limited to, fluorosurfactants such as ZONYL® UR and ZONYL® FS-62 (DuPont Canada Inc.), and ammonium fluoroalkylsulfonates such as Novec™ 4300 (3M Company).

It will be appreciated that it is common practice to make concentrated forms of the compositions to be diluted prior to use. For example, the composition may be manufactured in a more concentrated form and thereafter diluted with at least one solvent before use and/or during use. Dilution ratios may be in a range from about 0.1 part diluent:1 part composition concentrate to about 100 parts diluent:1 part composition concentrate. It should further be appreciated that the concentrated form can be substantially devoid of oxidizing agent(s) and the oxidizing agent(s) can be introduced to the concentrate or the diluted composition prior to use and/or during use.

The composition above may be easily formulated by the simple addition of the respective components and mixing to homogeneous condition. Furthermore, the composition may be readily formulated as single-package formulations or multi-part formulations that are mixed at or before the point of use. The individual parts of the multi-part formulation may be mixed at the tool or in a mixing region/area such as an inline mixer or in a storage tank upstream of the tool. It is contemplated that the various parts of the multi-part formulation may contain any combination of ingredients/constituents that when mixed together form the desired composition. The concentrations of the respective ingredients may be widely varied in specific multiples of the composition, i.e., more dilute or more concentrated, and it will be appreciated that the compositions can vary and alternatively comprise, consist or consist essentially of any combination of ingredients consistent with the disclosure herein.

According to a third aspect, the present disclosure relates to methods for removing chemical residue from a metal or dielectric surface by contacting the metal or dielectric surface with the composition of the second aspect. The composition may applied in any suitable manner to the metal or dielectric surface, for example, by spraying the composition on the surface, by dipping (in a static or dynamic volume of the composition) the surface, by contacting the surface with another material, for example, a pad, or fibrous sorbent applicator element, that has the composition absorbed thereon, by contacting the surface with a circulating composition, or by any other suitable means, manner or technique, by which the composition is brought into removal contact with the surface. The composition may be contacted with the surface for a sufficient time of from about 0.3 minute to about 60 minutes, or from about 0.5 minutes to about 30 minutes, at temperature in a range of from about 20° C. to about 100° C., or from about 30° C. to about 70° C. Such contacting times and temperatures are illustrative, and any other suitable time and temperature conditions may be employed that are efficacious to at least partially remove the chemical residue from the surface.

EXAMPLES

Example 1: Quaternary Ammonium Hydroxide Synthesis Procedure

In a pressure kettle, 3.50 lb N,N,N',N'-tetramethylethylenediamine was charged followed by addition of 8.07 lb deionized water. After purging the contents with nitrogen, 2.72 lb of ethylene oxide was added at a rate so as to keep the reaction temperature below 40° C. The reaction was allowed to continue for one hour then purged with nitrogen to remove unreacted ethylene oxide. Titration indicated about 55% of the amine nitrogen's were quaternized.

Example 2: Quaternary Ammonium Hydroxide Synthesis Procedure

In a manner similar to Example I, 5.00 lb of pentamethyldiethylenetriamine ("PMDETA") was reacted with 3.89 lb ethylene oxide in the presence of 11.52 lb deionized water at 45° C. maximum temperature. Titration indicated about 61% of the amine nitrogen's, or 1.9 nitrogen atoms per molecule, were quaternized. NMR spectra indicated quaternary nitrogen's formed in the same molecule on the nitrogen's bearing two methyl groups but not on the central nitrogen of PMDETA. Ethylene oxide which was in excess of two moles per PMDETA chained out to a limited extent on the hydroxyethyl group on the diquat terminus.

Examples 3A and 3B: Quaternary Ammonium Hydroxide Synthesis Procedure

3A: In a manner similar to Example I, 9.50 lb of N,N,N',N'-tetrakis(2-hydroxyethyl)ethylenediamine was reacted with 3.61 lb ethylene oxide in the presence of 10.81 lb deionized water at 39° C. maximum temperature. Titration indicated about 50% of the amine nitrogen's were quaternized. 3B: In a manner similar to Example 1, 9.03 lb of N,N,N',N'-tetrakis(2-hydroxyethyl)ethylenediamine was reacted with 8.42 lb ethylene oxide in the presence of 5.42 lb deionized water at 47° C. maximum temperature. Titration indicated about 52% of the amine nitrogen's were quaternized.

Example 4: Quaternary Ammonium Hydroxide Synthesis Procedure

In a manner similar to Example I, 2.40 lb of bis(2-dimethylaminoethyl)ether was reacted with 1.35 lb ethylene oxide in the presence of 5.00 lb deionized water at 40° C. maximum temperature. Titration indicated about 85% of the amine nitrogen's were quaternized.

Copper and aluminum substrates where exposed to Example 1, 2, 3A and 3B over 3 days and an indication of their reactivity was compared to state of the art quaternary ammonium hydroxides as shown below.

| Example | | I | II | III a | III b | THEMAH[a] | COH[b] |
|---|---|---|---|---|---|---|---|
| pH | | 13.4 | 13.4 | 13.5 | 13.5 | 13.3 | 13.5 |
| Corrosion to Cu | 1 d | 29 | 5 | 25 | 9 | 106 | 4 |
| | 2 d | 26 | 5 | 18 | 7 | 103 | 6 |
| | 3 d | 45 | 19 | 11 | 9 | 120 | 16 |
| Corrosion to Al | 1 d | 839 | 3515 | 2326 | 1954 | 1662 | 3038 |
| | 2 d | 796 | 4170 | 2445 | 1881 | 1580 | 2721 |
| | 3 d | 736 | 3096 | 2018 | 1908 | 1206 | 2568 |

[a] Tris(2-hydroxyethyl)methylammonium hydroxide,
[b] choline hydroxide

While the foregoing is directed to embodiments of the present disclosure, other and further embodiments of the disclosure may be devised without departing from the basic scope thereof, and the scope thereof is determined by the claims that follow.

The invention claimed is:

1. A quaternary ammonium hydroxide solution comprising the reaction product of (i) a polyamine having a formula:

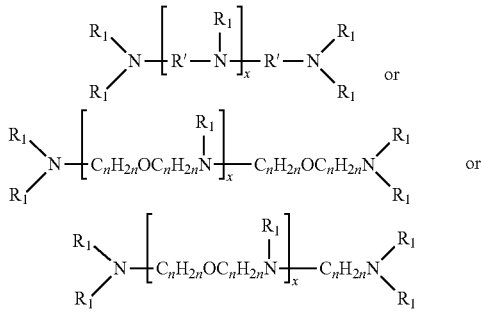

where each $R_1$ is independently hydrogen, an alkyl group, a cycloalkyl group, an aryl group, an alkyloxyalkyl group, a hydroxylated alkyl group, a hydroxylated alkyloxyalkyl group or two $R_1$ groups may be joined to form a cyclic amine, with the proviso that the $R_1$ groups are selected in such a combination that at least one tertiary nitrogen is formed and that each R1 group has less than 6 carbon atoms; x is 0 or an integer of 1 to 10; n is an integer of at least 2; R' is an alkyl group with 2 to 10 carbon atoms, an aryl group, alkaryl group, or unsaturated hydrocarbyl with 2 to 10 carbon atoms, or a group containing O or N in combination with C and H and may form a cyclic structure; and (ii) an organic oxirane having the formula

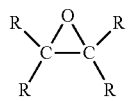

where each R is independently hydrogen, an alkyl group having 1 to 6 carbon atoms, an unsaturated alkyl group, an aryl group an aralkyl group or one or more R groups may form a cyclic structure containing 3 to 12 carbon atoms and optionally the R groups may contain one or more oxygen atoms wherein the concentration of quaternized amines in the quaternary ammonium hydroxide solution ranges from 10% by weight to 70% by weight, based on the total amount of the quaternized ammonium hydroxide solution.

2. The quaternary ammonium hydroxide solution of claim 1 wherein the polyamine is bis(3-dimethylaminopropyl) ether.

3. The quaternary ammonium hydroxide solution of claim 1 wherein the polyamine is bis(2-morpholinoethyl) ether.

4. The quaternary ammonium hydroxide solution of claim 1 wherein the polyamine is bis(2-dimethylaminoethyl) amine.

5. The quaternary ammonium hydroxide solution of claim 1 wherein the polyamine is N, N, N-tris(3-dimethylaminopropyl)amine.

6. The quaternary ammonium hydroxide solution of claim 1 wherein the polyamine is N, N, N', N''', N'''-pentamethyldiethylenetriamine.

7. The quaternary ammonium hydroxide solution of claim 1 wherein the polyamine is N, N, N', N''', N'''-pentamethyldipropylenetriamine.

8. The quaternary ammonium hydroxide solution of claim 1 wherein the organic oxirane is ethylene oxide.

9. The quaternary ammonium hydroxide solution of claim 1 wherein the organic oxirane is propylene oxide.

10. The quaternary ammonium hydroxide solution of claim 1 wherein the quaternary ammonium hydroxide solution contains 1 mole percent or more of quaternary ammonium compounds having at least two quaternary groups compared to the total moles of quaternary compounds.

11. The quaternary ammonium hydroxide solution of claim 1 further comprising water.

12. The quaternary ammonium hydroxide solution of claim 1 further comprising a miscible organic solvent.

13. A composition for removing chemical residue from a metal surface or dielectric surface comprising the quaternary ammonium hydroxide solution of claim 1.

14. A method for removing chemical residue from a metal surface or dielectric surface comprising contacting the metal surface or dielectric surface with the composition of claim 1.

15. A method of forming quaternary ammonium hydroxide solution of claim 1 comprising (i) contacting the polyamine with the organic oxirane in situ to convert the polyamine to a polyamine comprising a tertiary group and (ii) allowing the polyamine comprising the tertiary amine group to further react with the organic oxirane to form the quaternary ammonium hydroxide.

16. The method of claim 15 wherein the polyamine is N,N'-bis(2-aminoethyl)piperazine.

17. The method of claim 15 wherein the polyamine is N,N'-bis(3-aminopropyl)piperazine.

18. The method of claim 15 wherein the polyamine is bis(2-dimethylaminoethyl) ether.

* * * * *